(12) United States Patent
Annegarn et al.

(10) Patent No.: US 11,039,760 B2
(45) Date of Patent: Jun. 22, 2021

(54) DETECTION OF WALKING IN MEASUREMENTS OF THE MOVEMENT OF A USER

(71) Applicant: KONINKLIJKE PHILIPS N.V., Eindhoven (NL)

(72) Inventors: Janneke Annegarn, Eindhoven (NL); Warner Rudolph Theophile Ten Kate, Waalre (NL); Nicolaas Gregorius Petrus Den Teuling, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 473 days.

(21) Appl. No.: 15/114,095

(22) PCT Filed: Jan. 26, 2015

(86) PCT No.: PCT/EP2015/051426
§ 371 (c)(1),
(2) Date: Jul. 26, 2016

(87) PCT Pub. No.: WO2015/113915
PCT Pub. Date: Aug. 6, 2015

(65) Prior Publication Data
US 2017/0000384 A1 Jan. 5, 2017

(30) Foreign Application Priority Data
Jan. 30, 2014 (EP) .................................... 14153190

(51) Int. Cl.
*A61B 5/11* (2006.01)
*G01C 22/00* (2006.01)
*G06K 9/00* (2006.01)

(52) U.S. Cl.
CPC ............. *A61B 5/112* (2013.01); *A61B 5/1118* (2013.01); *A61B 5/1123* (2013.01);
(Continued)

(58) Field of Classification Search
CPC ...................................................... A61B 5/112
See application file for complete search history.

(56) References Cited

U.S. PATENT DOCUMENTS

| 8,206,325 B1 | 6/2012 | Najafi et al. |
| 2004/0228503 A1 | 11/2004 | Cutler |

(Continued)

FOREIGN PATENT DOCUMENTS

| CN | 103445792 A | 12/2013 |
| JP | H11347021 A | 12/1999 |

(Continued)

OTHER PUBLICATIONS

Ten Kate: "Fall Prevention-Monitoring Dynamic Gait Stability"; Technical Note TN-PR-TN 2009-00545, Nov. 2009, 28 Page Document.

(Continued)

*Primary Examiner* — Daniel L Cerioni
*Assistant Examiner* — Yasmeen S Warsi

(57) ABSTRACT

There is provided a method of processing measurements of acceleration to identify steps by a user, the method comprising obtaining measurements of acceleration from a device worn or carried by a user; analysing the measurements of acceleration to determine a value for a threshold that is to be used to identify steps by the user in measurements of acceleration; and using the determined value for the threshold to identify steps by the user in measurements of acceleration.

20 Claims, 12 Drawing Sheets

(52) U.S. Cl.
CPC ......... *G01C 22/006* (2013.01); *G06K 9/0053* (2013.01); *G06K 9/00348* (2013.01); *A61B 2562/0219* (2013.01)

(56) References Cited

U.S. PATENT DOCUMENTS

| | | |
|---|---|---|
| 2012/0101411 A1 | 4/2012 | Hausdorff et al. |
| 2013/0085677 A1 | 4/2013 | Modi et al. |
| 2013/0166198 A1* | 6/2013 | Funk .................. G01C 21/165 701/446 |
| 2013/0325396 A1 | 12/2013 | Yuen et al. |
| 2014/0066816 A1 | 3/2014 | McNames et al. |

FOREIGN PATENT DOCUMENTS

| | | |
|---|---|---|
| JP | 2007148702 A | 6/2007 |
| JP | 2011152360 A | 8/2011 |
| JP | 2013532009 A | 8/2013 |
| JP | 2013532020 A | 8/2013 |
| WO | 2007105648 A1 | 9/2007 |
| WO | 2009101566 A1 | 8/2009 |
| WO | 2011004322 A1 | 1/2011 |
| WO | 2011151740 A2 | 12/2011 |
| WO | 2011157607 A1 | 12/2011 |
| WO | 2012050908 A2 | 4/2012 |
| WO | 2013024461 A1 | 2/2013 |
| WO | WO-2013169755 A2 * | 11/2013 |

OTHER PUBLICATIONS

Moe-Nilssen et al: "Estimation of Gait Cycle Characteristics by Trunk Accelerometry"; Journal of Biomechanics, vol. 37, 2004, pp. 121-126.

* cited by examiner

DETECTION OF WALKING IN MEASUREMENTS OF THE MOVEMENT OF A USER

CROSS-REFERENCE TO PRIOR APPLICATIONS

This application is the U.S. National Phase application under 35 U.S.C. § 371 of International Application No. PCT/EP2015/051426, filed on Jan. 26, 2015, which claims the benefit of European Patent Application No. 14153190.5, filed on Jan. 30, 2014. These applications are hereby incorporated by reference in their entirety herein.

TECHNICAL FIELD OF THE INVENTION

The invention relates to the processing of measurements of the movement of a user, and in particular relates to a method and device for processing measurements of the movement of a user to detect when the user is walking.

BACKGROUND TO THE INVENTION

Many devices, such as physical activity monitors, are currently available that measure the movements of a user. These devices process the measurements to detect the foot steps of the user and detect when the user is walking.

Various characteristics of a user's walking can be used by clinicians as a tool to assess the mobility of the user. In some cases, the characteristics can be used to assess a user's risk of falling.

Many of these devices have been developed to assess walking characteristics in a standardised setting, such as a healthcare clinic, but they therefore cannot provide an accurate reflection of the user's functional ability in their home environment or changes in the user's ability over time. Therefore some devices are being developed that can be worn or carried by the user in their home environment and that can provide an indication of when the user is walking and characteristics of the user's walking Preferably these devices should be as unobtrusive as possible for the user, and thus some devices are provided so that they can be worn on the user's arm/wrist, worn at their waist or on their chest, or, more preferably, worn as a pendant around the user's neck.

It will be appreciated that where the output of the device is used as a clinical assessment tool or as an input to a fall risk assessment algorithm, it is important that the device accurately detects walking in the measurements of the movement of the user, since if certain activities are incorrectly classified by the device as walking, then the subsequent assessment of the user's mobility or fall risk may be inaccurate or unreliable.

An algorithm for a device that is worn by a user for detecting walking (and other forms of traversing, such as running, hopping, etc.) has been described in WO 2011/004322. In this algorithm, which was presented as having specific application to determining the fall risk of a user, measurements of the motion of the user are collected, and the measurements are processed to identify step boundaries (which can be defined as the moment the user's heel strikes the ground) corresponding to a maximum value in a cluster of measurements that exceed a threshold.

It has been found that this algorithm provides a very high precision in detecting walking, even in a device that is worn as a pendant. However, the algorithm is not always 100% accurate and further gains in sensitivity and precision are desired. There is therefore a need for improved algorithms for detecting walking in measurements of the movement of a user.

SUMMARY OF THE INVENTION

According to a first aspect of the invention, there is provided a method of processing measurements of acceleration to identify steps by a user, the method comprising obtaining measurements of acceleration from a device worn or carried by a user; analysing the measurements of acceleration to determine a value for a threshold that is to be used to identify steps by the user in measurements of acceleration; and using the determined value for the threshold to identify steps by the user in measurements of acceleration.

Preferably, the step of analysing the measurements of acceleration comprises determining one or more characteristics from the measurements of acceleration; and determining a value for a threshold that is to be used to identify steps by the user from the one or more characteristics. Preferably the step of determining one or more characteristics comprises determining a mean of the measurements and/or standard deviation.

The step of determining one or more characteristics from the measurements of acceleration preferably comprises determining one or more characteristics of the measurements of acceleration, the norm of the measurements of the acceleration, the derivative of the acceleration or the norm of the derivative of the acceleration.

In some embodiments the step of determining a value for a threshold comprises calculating $|grav|+ThresFac*(Mean-|grav|+Std)$ where $|grav|$ is acceleration due to gravity, ThresFac is a constant, Mean is the mean of the measurements of acceleration or the mean of the norm of the measurements of acceleration and Std is the standard deviation of the measurements of acceleration or the mean of the norm of the measurements of acceleration.

In other embodiments the step of determining a value for a threshold comprises calculating two thresholds using $Mean+ThresFacIn*Std$ and $Mean-ThresFacOut*Std$ where ThresFacIn and ThreshFacOut are constants, Mean is the mean of the derivative of the measurements of acceleration or the mean of the norm of the derivative of the measurements of acceleration and Std is the standard deviation of the derivative of the measurements of acceleration or the mean of the norm of the derivative of the measurements of acceleration.

In some embodiments the method further comprises the steps of identifying a first step and a last step for a walking part from the steps identified in the measurements of acceleration; and repeating the steps of analysing and using on the measurements of acceleration corresponding to the walking part to identify steps by the user.

In some embodiments, the step of using the determined value for the threshold to identify steps by the user in measurements of acceleration comprises using the determined value for the threshold to identify clusters of measurements in which at least some of the measurements of acceleration or the norm of the measurements of acceleration meet the determined value; and identifying a step as a measurement at or near an extremum measurement in each cluster.

In other embodiments, the step of using the determined value for the threshold to identify steps by the user in measurements of acceleration comprises using the determined value for the threshold to identify clusters of measurements in which at least some of the values of the derivative of the measurements of acceleration or the norm of the derivative of the measurements of acceleration meet the determined value; and identifying a step as a measurement at or near an extremum value of the derivative or the norm of the derivative in each cluster.

In some embodiments, for a walking part comprising a series of steps identified in the measurements of acceleration, the method further comprises testing the identified steps for regularity; adding a step by the user to the series of steps if it is determined from the result of the step of testing that a step by the user has been missed; and removing a step by the user from the series of steps if it is determined from the result of the step of testing that there is a duplicated step by the user.

In some embodiments, the step of testing the identified steps for regularity comprises determining a step time for each pair of consecutive steps in the series of steps as the time between the consecutive steps; determining a central step time as the average of the determined step times; and identifying a step time as regular if the step time is within a threshold amount of the central step time.

Preferably, the step of testing the identified steps for regularity further comprises if a step time for a particular pair of consecutive steps is not within a threshold amount of the central step time, determining the step time between one of the pair of consecutive steps and a step neighbouring the other one of the pair of consecutive steps; identifying the step time for the particular pair of consecutive steps as regular if the determined step time between the one of the pair of consecutive steps and the step neighbouring the other one of the pair of consecutive steps is within a threshold amount of twice the central step time; and otherwise identifying the step time for the particular pair of consecutive steps as irregular.

Preferably, the step of testing the identified steps for regularity further comprises if the step time for a particular pair of consecutive steps is identified as irregular, comparing the step time to the central step time; determining that a step between the pair of consecutive steps has been missed if the step time is greater than the central step time; and determining that a step in the pair of consecutive steps is a duplicate if the step time is less than the central step time.

In alternative embodiments the step of testing the identified steps for regularity comprises determining a step time for each pair of consecutive steps in the series of steps as the time between the consecutive steps; for the smallest determined step time, computing a first variance as the variance of the step times for each pair of consecutive steps, computing a second variance as the variance of the step times when the first step forming the pair of steps with the smallest determined step time is omitted, and computing a third variance as the variance of the step times when the second step forming the pair of steps with the smallest determined step time is omitted; removing the first step forming the pair of steps with the smallest determined step time if the second variance is the smallest variance of the first variance, the second variance and the third variance; and removing the second step forming the pair of steps with the smallest determined step time if the third variance is the smallest variance of the first variance, the second variance and the third variance.

In some embodiments, for a walking part comprising a series of steps identified in the measurements of acceleration, the method further comprises discarding the walking part if it has a duration less than a threshold duration.

In some embodiments, for a walking part comprising a series of steps identified in the measurements of acceleration, the method further comprises evaluating a stride regularity of the walking part.

In some embodiments the step of evaluating a stride regularity of the walking part comprises determining the autocorrelation of the walking part.

In some embodiments the step of evaluating a stride regularity of the walking part comprises filtering the determined autocorrelation of the walking part to identify a stride peak.

In some embodiments the step of evaluating a stride regularity of the walking part comprises if a stride peak is identified, calculating an autocovariance ratio from the stride peak and the autocorrelation at zero lag; comparing the autocovariance ratio to a threshold; and determining the walking part relates to walking if the autocovariance ratio is greater than the threshold.

In preferred embodiments, the step of evaluating a stride regularity of the walking part comprises evaluating the stride regularity for a portion of the walking part.

In some embodiments, for a walking part comprising a series of steps identified in the measurements of acceleration, the method further comprises determining an activity level for the user from the measurements of acceleration corresponding to the walking part; and discarding the walking part if the activity level of the user indicates that the user is not walking.

In some embodiments the step of determining an activity level for the user from the measurements of acceleration corresponding to the walking part comprises calculating the activity level from the variance of the acceleration.

In some embodiments the method comprises determining if the user is walking or not walking by comparing the determined activity level to one or more thresholds or a range.

In some embodiments, for a walking part comprising a series of steps identified in the measurements of acceleration, the method further comprises determining if the walking part corresponds to the user walking up or down stairs; and discarding the walking part if it is determined that the walking part corresponds to the user walking up or down stairs.

In some embodiments the step of determining if the walking part corresponds to the user walking up or down stairs comprises obtaining measurements of the air pressure from the device worn or carried by the user; and processing the obtained measurements of air pressure to determine if there has been a change in height consistent with the user walking up or down stairs during the walking part.

In some embodiments the step of processing the obtained measurements of air pressure comprises filtering the measurements of air pressure; comparing a change in pressure in the filtered measurements over a predetermined time period to a threshold value; and determining that the walking part corresponds to the user walking up or down stairs if the change in pressure over the predetermined time period is greater than the threshold value.

In some embodiments the step of filtering the measurements of air pressure comprises applying a median filter to the air pressure measurements.

According to a second aspect of the invention, there is provided an apparatus for processing measurements of acceleration to identify steps by a user, the apparatus comprising a processing unit configured to obtain measurements of acceleration from a device worn or carried by a user; analyse the measurements of acceleration to determine a value for a threshold that is to be used to identify steps by the user in measurements of acceleration; and use the determined value for the threshold to identify steps by the user in measurements of acceleration.

Various embodiments of the apparatus are also contemplated in which the processing unit is further configured to implement the method embodiments described above.

In some embodiments, the apparatus is part of the device that is to be worn or carried by a user, with the device comprising an accelerometer for providing measurements of acceleration.

In alternative embodiments, the apparatus is remote from the device that is to be worn or carried by a user, with the device comprising an accelerometer for providing measurements of acceleration.

According to another aspect, there is provided a method of processing a signal representing a series of steps identified in measurements of acceleration obtained from a device worn or carried by a user, the method comprising testing the identified steps for regularity; adding a step by the user to the series of steps if it is determined from the result of the step of testing that a step by the user has been missed; and removing a step by the user from the series of steps if it is determined from the result of the step of testing that there is a duplicated step by the user.

In some embodiments, the step of testing the identified steps for regularity comprises determining a step time for each pair of consecutive steps in the series of steps as the time between the consecutive steps; determining a central step time as the average of the determined step times; and identifying a step time as regular if the step time is within a threshold amount of the central step time.

In some embodiments the step of testing the identified steps for regularity further comprises if a step time for a particular pair of consecutive steps is not within a threshold amount of the central step time, determining the step time between one of the pair of consecutive steps and a step neighbouring the other one of the pair of consecutive steps; identifying the step time for the particular pair of consecutive steps as regular if the determined step time between the one of the pair of consecutive steps and the step neighbouring the other one of the pair of consecutive steps is within a threshold amount of twice the central step time; and otherwise identifying the step time for the particular pair of consecutive steps as irregular.

In some embodiments the step of testing the identified steps for regularity further comprises if the step time for a particular pair of consecutive steps is identified as irregular, comparing the step time to the central step time; determining that a step between the pair of consecutive steps has been missed if the step time is greater than the central step time; and determining that a step in the pair of consecutive steps is a duplicate if the step time is less than the central step time.

In alternative embodiments, the step of testing the identified steps for regularity comprises determining a step time for each pair of consecutive steps in the series of steps as the time between the consecutive steps; for the smallest determined step time, computing a first variance as the variance of the step times for each pair of consecutive steps, computing a second variance as the variance of the step times when the first step forming the pair of steps with the smallest determined step time is omitted, and computing a third variance as the variance of the step times when the second step forming the pair of steps with the smallest determined step time is omitted; removing the first step forming the pair of steps with the smallest determined step time if the second variance is the smallest variance of the first variance, the second variance and the third variance; and removing the second step forming the pair of steps with the smallest determined step time if the third variance is the smallest variance of the first variance, the second variance and the third variance.

According to another aspect, there is provided an apparatus for processing a signal representing a series of steps identified in measurements of acceleration obtained from a device worn or carried by a user, the apparatus comprising a processing unit configured to test the identified steps for regularity; add a step by the user to the series of steps if it is determined from the result of the step of testing that a step by the user has been missed; and remove a step by the user from the series of steps if it is determined from the result of the step of testing that there is a duplicated step by the user.

Various embodiments of the apparatus are also contemplated in which the processing unit is further configured to implement the method embodiments described above.

According to a further aspect, there is provided a method of processing a signal representing a series of steps identified in measurements of acceleration obtained from a device worn or carried by a user, the series of steps corresponding to a walking part, the method comprising evaluating a stride regularity of the walking part.

In some embodiments the step of evaluating a stride regularity of the walking part comprises determining the autocorrelation of the walking part.

In some embodiments the step of evaluating a stride regularity of the walking part comprises filtering the determined autocorrelation of the walking part to identify a stride peak.

In some embodiments the step of evaluating a stride regularity of the walking part comprises if a stride peak is identified, calculating an autocovariance ratio from the stride peak and the autocorrelation at zero lag; comparing the autocovariance ratio to a threshold; and determining the walking part relates to walking if the autocovariance ratio is greater than the threshold.

In some embodiments the step of evaluating a stride regularity of the walking part comprises evaluating the stride regularity for a portion of the walking part.

According to a further aspect, there is provided an apparatus for processing a signal representing a series of steps identified in measurements of acceleration obtained from a device worn or carried by a user, the series of steps corresponding to a walking part, the apparatus comprising a processing unit configured to evaluate a stride regularity of the walking part.

Various embodiments of this apparatus are also contemplated in which the processing unit is further configured to implement the method embodiments described above.

According to yet another aspect, there is provided a method of processing a signal representing a series of steps identified in measurements of acceleration obtained from a device worn or carried by a user, the series of steps corresponding to a walking part, the method comprising determining an activity level for the user from the measurements of acceleration corresponding to the walking part; and discarding the walking part if the activity level of the user indicates that the user is not walking.

In some embodiments the step of determining an activity level for the user from the measurements of acceleration corresponding to the walking part comprises calculating the activity level from the variance of the acceleration.

In some embodiments the method comprises determining if the user is walking or not walking by comparing the determined activity level to one or more thresholds or a range.

According to yet another aspect, there is provided an apparatus for processing a signal representing a series of steps identified in measurements of acceleration obtained from a device worn or carried by a user, the series of steps corresponding to a walking part, the apparatus comprising a processing unit configured to determine an activity level for the user from the measurements of acceleration corresponding to the walking part; and discard the walking part if the activity level of the user indicates that the user is not walking.

Various embodiments of this apparatus are also contemplated in which the processing unit is further configured to implement the method embodiments described above.

According to another aspect, there is provided a method of processing a signal representing a series of steps identified in measurements of acceleration obtained from a device worn or carried by a user, the series of steps corresponding to a walking part, the method comprising determining if the walking part corresponds to the user walking up or down stairs; and discarding the walking part if it is determined that the walking part corresponds to the user walking up or down stairs.

In some embodiments the step of determining if the walking part corresponds to the user walking up or down stairs comprises obtaining measurements of the air pressure from the device worn or carried by the user; and processing the obtained measurements of air pressure to determine if there has been a change in height consistent with the user walking up or down stairs during the walking part.

In some embodiments the step of processing the obtained measurements of air pressure comprises filtering the measurements of air pressure; comparing a change in pressure in the filtered measurements over a predetermined time period to a threshold value; and determining that the walking part corresponds to the user walking up or down stairs if the change in pressure over the predetermined time period is greater than the threshold value.

In some embodiments the step of filtering the measurements of air pressure comprises applying a median filter to the air pressure measurements.

According to yet another aspect, there is provided an apparatus for processing a signal representing a series of steps identified in measurements of acceleration obtained from a device worn or carried by a user, the series of steps corresponding to a walking part, the apparatus comprising a processing unit configured to determine if the walking part corresponds to the user walking up or down stairs; and discarding the walking part if it is determined that the walking part corresponds to the user walking up or down stairs.

Various embodiments of this apparatus are also contemplated in which the processing unit is further configured to implement the method embodiments described above.

According to a final aspect of the invention, there is provided a computer program product having computer readable code embodied therein, the computer readable code being configured such that, on execution by a suitable processing unit or computer, the processing unit or computer performs the method according to any of the aspects of embodiments described above.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1:
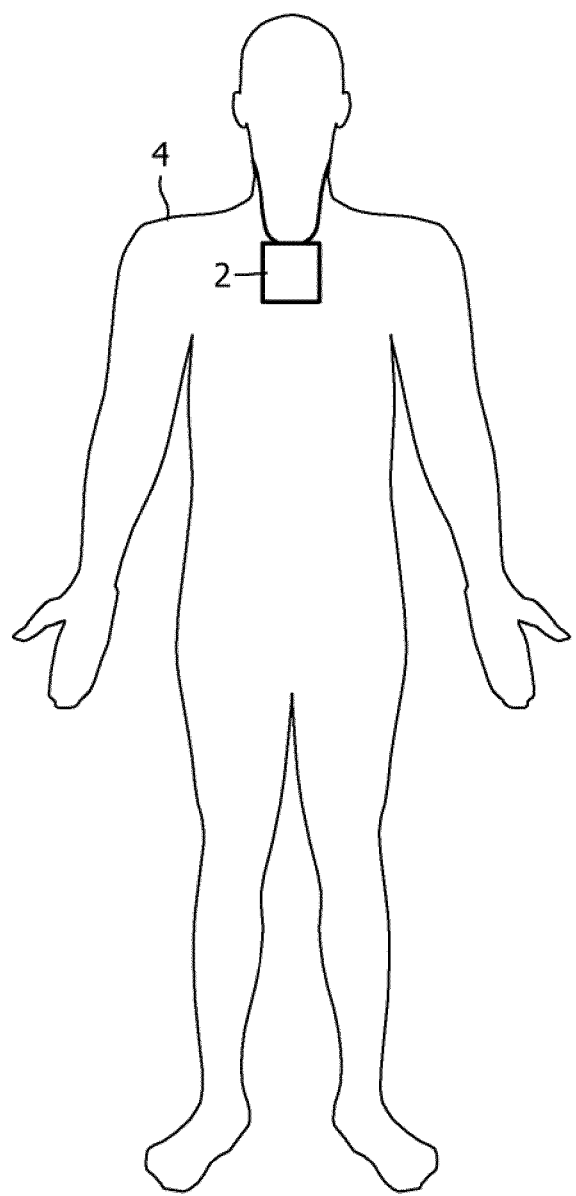
FIG. 1 is an illustration of a device according to an embodiment of the invention being worn by a user.
Figure 2:
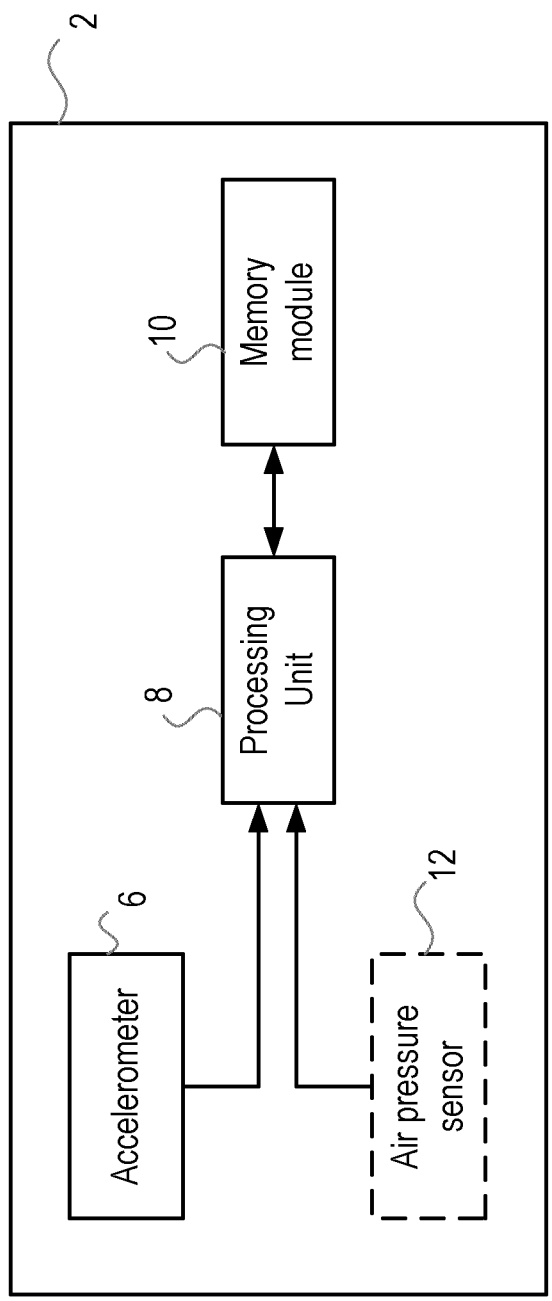
FIG. 2 is a block diagram of a device according to an embodiment of the invention.

FIG. 1 shows a device 2 in the form of a pendant being worn around the neck of a user 4 and FIG. 2 is a block diagram of the device 2. In some embodiments the device 2 is an activity monitor that monitors the physical activity of the user 4, for example for personal fitness purposes, or for supporting injury or fall prevention, for example during walking. Further the step/walking detection algorithms may be used in a device or system that uses gait parameters as a biometric for identifying an individual or in a device or system for detecting other forms of traversing to walking, such as running, hopping, etc.). In other embodiments, the device 2 can be used for other purposes, for example it can be a step counter, a velocity monitor or a stability monitor.

The device 2 comprises at least one movement sensor 6 that measures the movements of the device 2. Preferably the at least one movement sensor 6 comprises an accelerometer 6 that measures the magnitude and direction of the acceleration acting on the device 2. The accelerometer 6 measures the accelerations in three dimensions and outputs a signal for three (e.g. x, y and z) axes indicating the magnitude of the acceleration acting along that axis over time. The accelerometer 6 measures the acceleration at a predetermined sampling frequency, for example 50 Hz, although other sampling frequencies can be used.

The device 2 further comprises a processing unit 8 that receives the acceleration measurements from the accelerometer 6 and processes the measurements to identify when the user 4 is walking. The device 2 also comprises a memory module 10 that can be used to store computer readable code or instructions for execution by the processing unit 8 in order to cause the processing unit 8 to process the acceleration measurements according to the invention. The memory module 10 can also be used to store the acceleration measurements before, during and after the processing by the processing unit 8.

Although in the preferred embodiment of the invention the device 2 is in the form of a pendant to be worn on a cord or thread around the neck of a user 4, it will be appreciated that the device 2 can be implemented in alternative forms that are to be worn on different parts of the body of the user 4, such as at the waist, on the chest, arm, wrist, leg or ankle. In some of these embodiments, it may be necessary to modify the processing used to detect the footsteps or walking of the user 4 in view of the different movements/accelerations observed when the device 2 is placed at one of these alternative locations. These modifications are mentioned in the appropriate places below.

In this illustrated embodiment of the invention, the device 2 comprises a single unit that is worn by the user 4 and that collects and processes the movement measurements. In alternative embodiments, the processing of the measurements can be performed in a unit that is remote from the sensors (for example a unit that is worn on a different part of the body of the user 4, a base unit that can be located in the user's home, or a remote server located in the premises of a healthcare service provider), in which case the device 2 will comprise a sensor unit to be worn by the user 4 that comprises suitable transmitter or transceiver circuitry for transmitting the measurements to the remote unit. In this embodiment, there is no need for the user-worn sensor unit to include a processing unit that is capable of processing the measurements to detect the user's footsteps or walking.

In further embodiments, some of which are referenced further below, the device 2 may comprise one or more additional sensors for measuring the movement and/or orientation of the user 4. For example, the device 2 may comprise an air pressure sensor (barometer) 12 for measuring the air pressure at the device 2, and the processing unit 8 can process the air pressure measurements to obtain a measure of an altitude or altitude change/height change of the device 2. Other possible sensors include a gyroscope that can output a signal that can be processed to determine the orientation and/or change in orientation of the device 2, a magnetometer for measuring the Earth's magnetic field and that can be used to determine the direction or heading of the device 2, a location sensor, for example a satellite positioning system receiver (e.g. a Global Positioning System, GPS, receiver) for determining the location of the device 2.

It will be appreciated that in practical implementations, the device 2 may comprise other or further components to those shown in FIG. 2 and described above, such as a user interface that allows the user to activate and/or operate the device 2, and a power supply, such as a battery, for powering the device 2.

Figure 3:
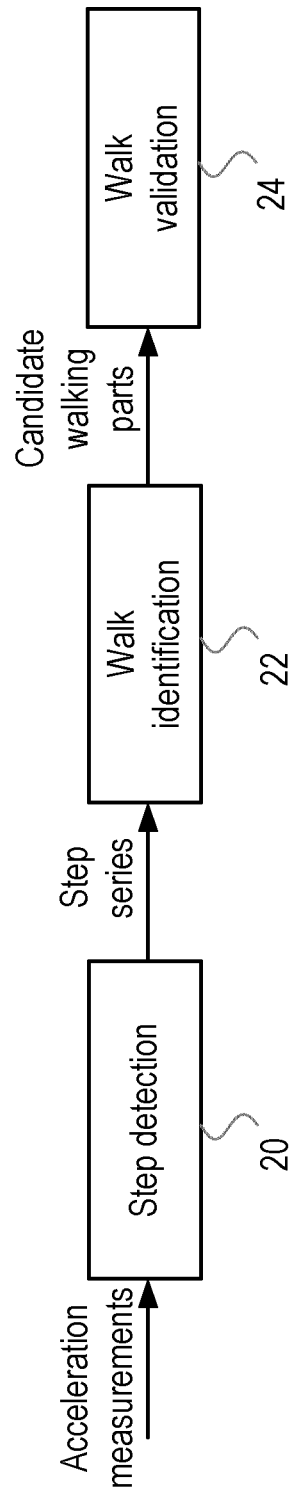
FIG. 3 outlines the processing steps in an exemplary algorithm according to some embodiments of the invention.

FIG. 3 outlines the processing steps in an algorithm used by the processing unit 8 according to some embodiments of the invention to determine when the user 4 is walking (i.e. to determine which parts of the input sensor signals correspond to the user walking) The overall aim of the algorithm is to detect the start and end times of periods of time in which the user is walking Each such period of time is referred to herein as a 'walking part'.

Figure 4:
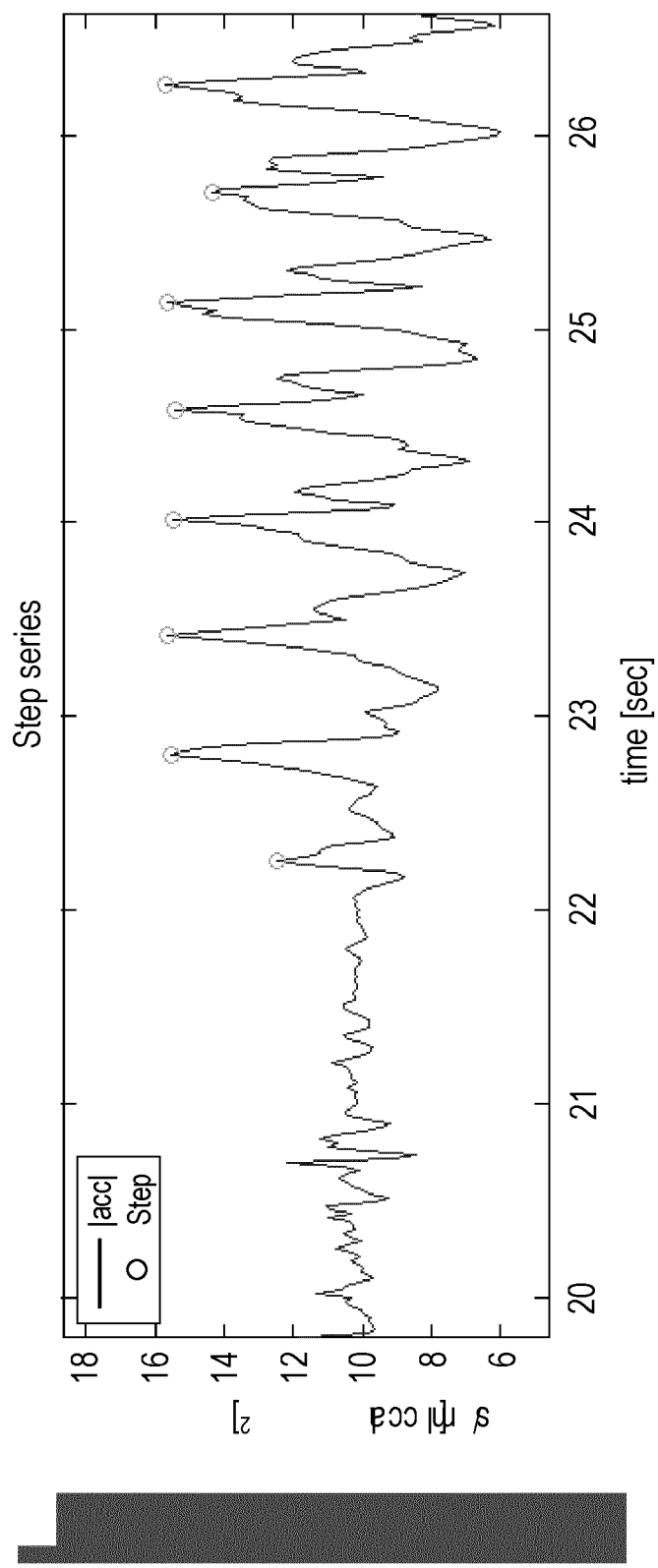
FIG. 4 is a plot indicating an exemplary step series signal.

In the first part of the algorithm, block 20, the movement measurements (e.g. acceleration measurements) are processed to detect the steps by the user 4. The output of this block 20 is a step series (i.e. a signal indicating the timing of the detected steps), an example of which is shown in FIG. 4, with the circles indicating identified steps. The step series is passed to a second block 22 that discards series of identified steps that do not have a sufficient duration to be considered walking (e.g. the user may walk from one room to another and/or stand up from a chair and perform a few steps to reach something and these steps should not be considered as consistent or regular walking (at least for the purposes of fitness monitoring or fall risk assessment)). The output of the second block 22, which is a signal representing one or more candidate walking parts, is passed to a third block 24 that validates each candidate walking part to determine whether it should be correctly classified as walking.

The various parts of the algorithm will now be described in more detail.

In the step detection block 20, a step (footstep) can be defined as the point in time that the heel of the user's swing leg strikes the ground (referred to as a heel strike, HS) during walking Some of the techniques described below for step detection on which aspects of the invention are based are described in WO 2011/004322.

For accelerometers 6 that are rigidly attached to the upper body of a user 4, a heel strike (or step boundary as it is also referred to herein) is usually found by observing the 'zero' crossing of the vertical acceleration. Of course, it will be appreciated that the actual "crossing" will be through 1 g (9.81 ms$^{-2}$) since gravity is always acting on the user 4. The vertical acceleration can be determined by determining the orientation of the accelerometer 6 and extracting the vertical component of acceleration—although for rigidly mounted accelerometers, the accelerometer reading along the coordinate axis corresponding to vertical usually provides a sufficient approximation.

However, in preferred embodiments in which the device 2 is in the form of a pendant, the device 2 (and therefore the accelerometer 6) is free to move relative to the user 4, which means that the accelerometer coordinate system also moves relative to the user 4. In this case, the norm of the acceleration signal can be observed and heel strikes typically show up in this norm as large peaks. Thus, in the step detection part of the algorithm, the acceleration measurements/signal is searched for peaks that could correspond to heel strikes.

Figure 5:
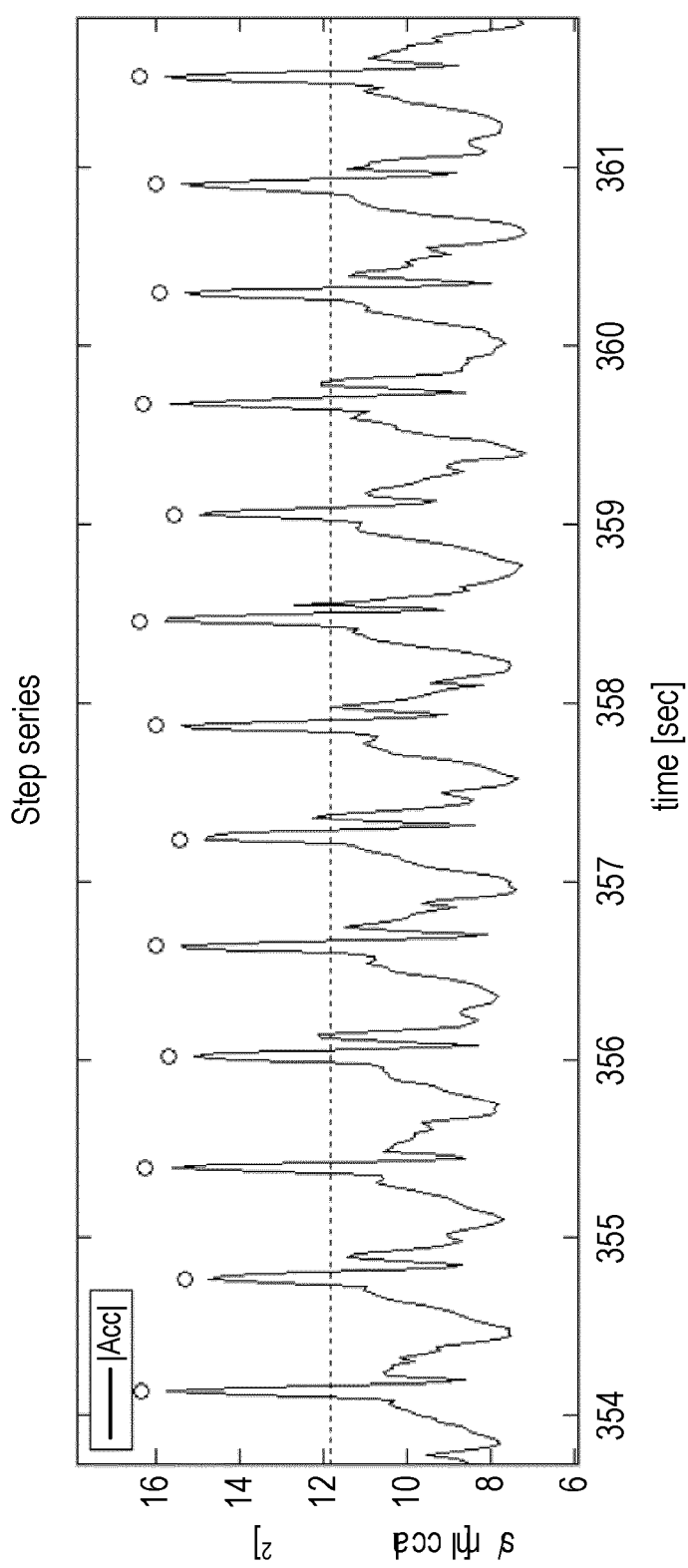
FIG. 5 is a plot illustrating measurements from an accelerometer that is in a pendant worn around a user's neck with step boundaries identified.

In some simple embodiments, any peaks (i.e. local maxima) in the acceleration signal (or the norm of the acceleration signal) that exceed a threshold value can be considered to be possible steps. An example of the norm of an acceleration signal, denoted as |acc|, is shown in FIG. 5 in which possible heel strike events where the norm of the acceleration exceeds a threshold are marked.

In some other simple embodiments (that are particularly useful when the device 2—or at least the accelerometer 6—is located on the lower part of the body of the user 4), the derivative of the acceleration signal (or the norm of the derivative of the acceleration signal) is determined and the derivative is searched for peaks exceeding a threshold value (or searched for minima falling below a threshold value in some cases described below) that correspond to a heel strike event. The derivative of the acceleration is referred to herein as 'jerk'. The derivative of the acceleration can be computed by taking the difference between subsequent acceleration sample values and multiplying by the sampling frequency, $f_s$, or dividing by the sampling time, $1/f_s$ (although the multiplication or division can be omitted to reduce computation effort if required).

In more preferred embodiments, clusters of samples in the acceleration or jerk signal are identified and the maximum value (or another value close to the maximum value) in each cluster is identified as a step boundary. In particular, the signal is analysed to identify regions of samples over which at least some of the samples in the acceleration signal (or the norm of the acceleration, the jerk or the norm of the jerk) are above (or below, as appropriate) a threshold.

In a first exemplary implementation, a cluster can correspond to a set of samples that exceed a threshold value (e.g. 2 ms$^{-2}$ above gravity, i.e. ~12 ms$^{-2}$). In a second exemplary implementation, a cluster can correspond to a set of samples that exceed a threshold value, with a small gap of samples that do not exceed the threshold being permitted, provided that the size of the gap is below a predetermined limit, threshold$_{gap}$. The predetermined limit is preferably less than a typical time between steps, which is around 0.5 seconds. An exemplary cluster of this nature can be seen between times 358 and 359 of FIG. 5.

In a third exemplary implementation, instead of using a single threshold to identify samples that form part of a cluster, two thresholds can be used. This introduces a hysteresis—a sample exceeding the first threshold indicates the start of a cluster and the first sample falling below the second threshold indicates the end of the cluster. A minimum time duration (possibly related to the step time—the time between two successive steps) between the start and end of the cluster can be applied if required. The use of two thresholds is particularly useful when the jerk of the acceleration signal is analysed to identify the step boundaries.

Figure 6:
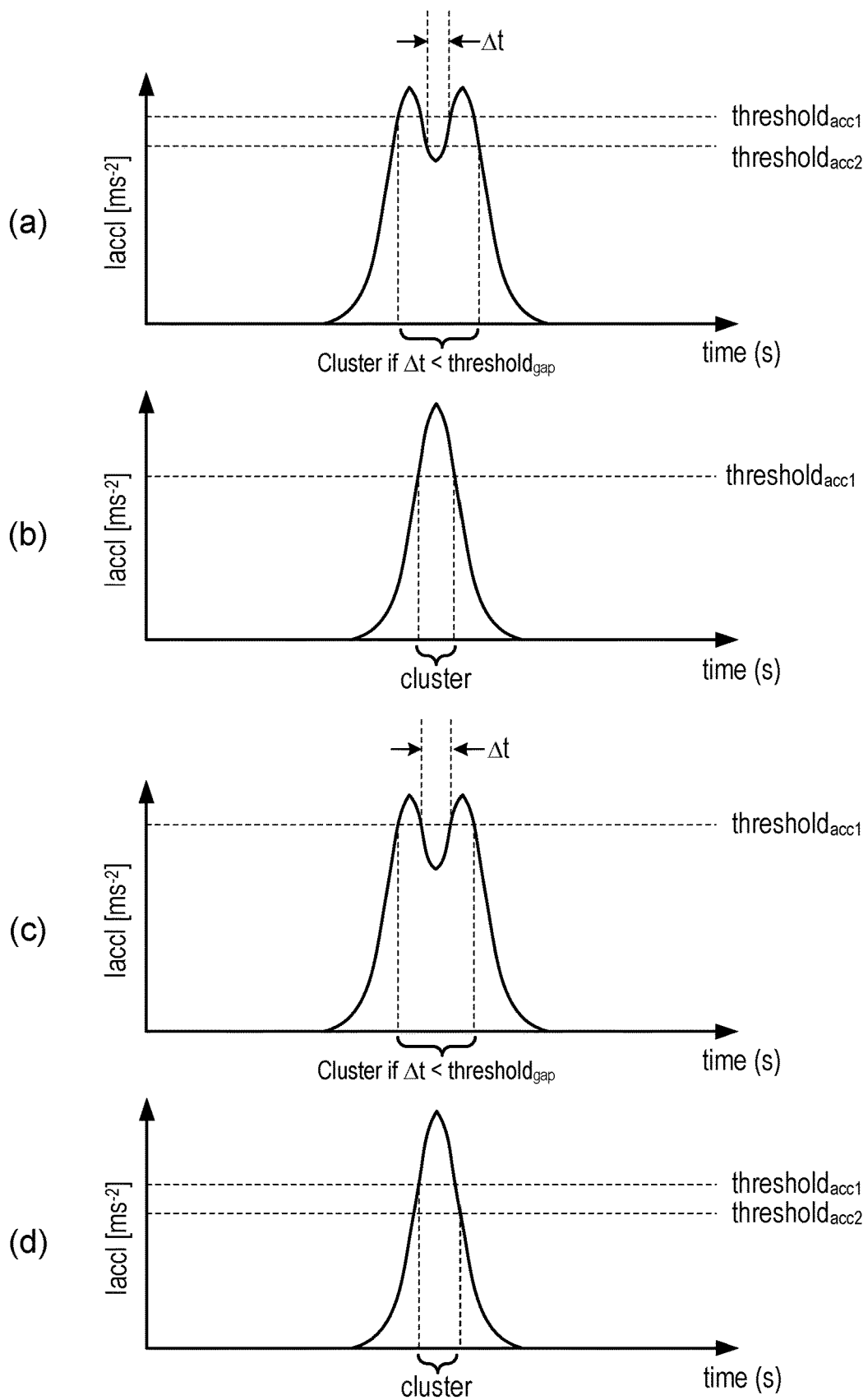
FIG. 6 is a series of graphs illustrating the detection of clusters according to some embodiments.

The graphs in FIG. 6 illustrate how clusters can be identified in various exemplary acceleration signals according to the implementations described above. The general case is shown in FIG. 6(*a*), where two thresholds threshold$_{acc1}$ and threshold$_{acc2}$ are applied to the samples and a gap of maximum duration threshold$_{gap}$ where the samples do not exceed the first threshold is permitted. In FIG. 6(*a*), the gap is denoted $\Delta t$, and if $\Delta t$<threshold$_{gap}$, a cluster will be found.

FIG. 6(*b*) illustrates the first exemplary implementation of cluster identification described above where all samples are required to exceed a threshold to identify a cluster (i.e. the cluster detection in FIG. 6(*b*) corresponds to threshold$_{acc1}$=threshold$_{acc2}$ and with no gap being permitted in the general case of FIG. 6(*a*)).

FIG. 6(*c*) illustrates the second exemplary implementation of cluster identification described above where a gap of samples that do not exceed the threshold is permitted in a cluster (i.e. the cluster detection in FIG. 6(*c*) corresponds to threshold$_{acc1}$=threshold$_{acc2}$ and threshold$_{gap}$=Y (where Y is a positive, non-zero, value) in the general case of FIG. 6(*a*)).

FIG. 6(*d*) illustrates the third exemplary implementation of cluster identification described above where two thresholds are used (i.e. the cluster detection in FIG. 6(*d*) corresponds to threshold$_{acc1}$≠threshold$_{acc2}$ with no gap being permitted in the general case of FIG. 6(*a*)).

Figure 7:
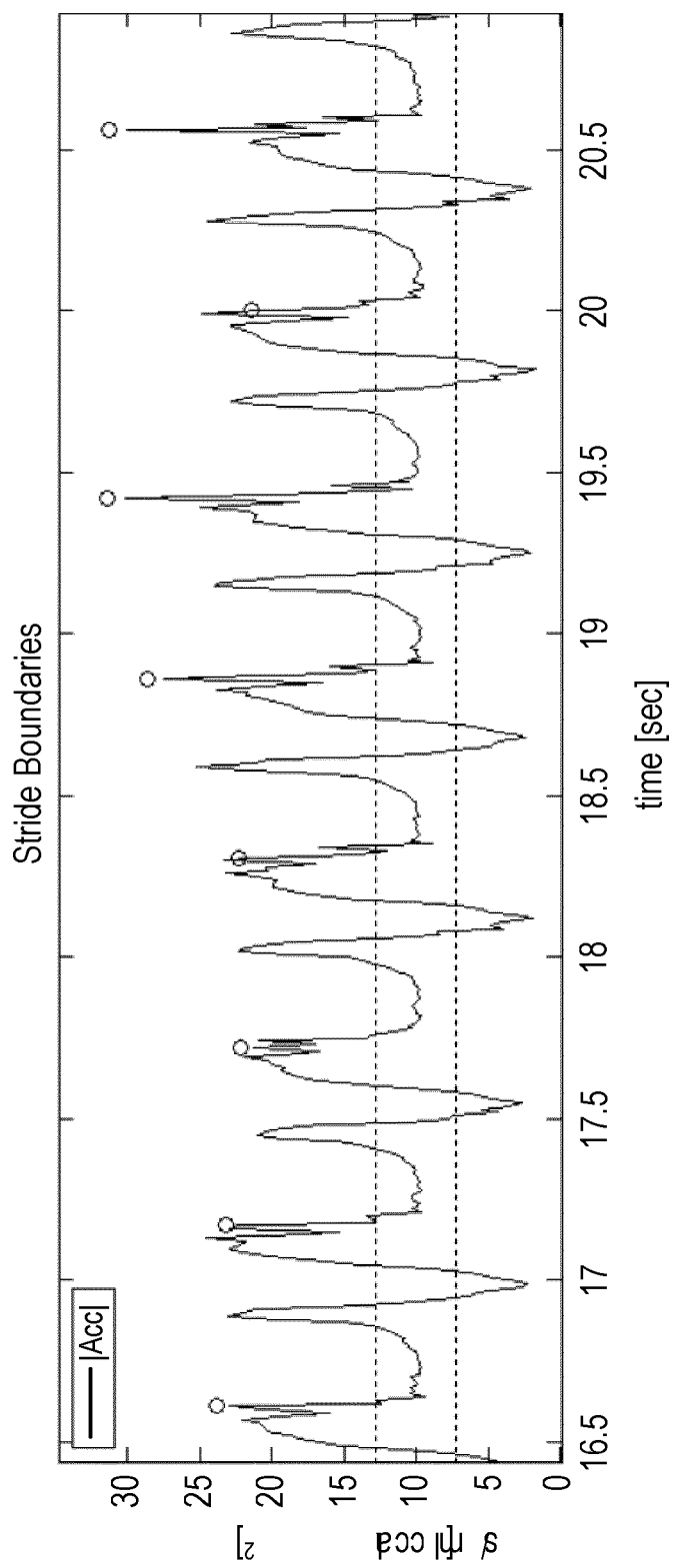
FIG. 7 is a plot illustrating measurements from an accelerometer that is worn on a user's ankle.

The above clustering techniques provide generally useful estimates of heel strikes for accelerometers 6 that are attached to the upper body of the user 4. If the accelerometer 6 is attached at or to the lower body of the user 4 (for example the ankle), then if acceleration is considered, then usually two clusters appear per step, or actually per stride, as shown in FIG. 7 (it will be noted that FIG. 7 also illustrates the use of two thresholds). Since the accelerometer signal is observed at the ankle, the period of a stride (i.e. a step with both the left foot and the right foot) is seen. One cluster corresponds to the lifting of the foot, and the other corresponds to the heel strike, with the unique minimum in each cluster corresponding to the swing phase. It can be difficult to decide which of the two the heel strike is. However, it can also be observed that a single minimum occurs per step, and if the device 2 is to be used on the lower body of the user 4, then the algorithm can search the norm of the acceleration signal for the minimum value (or a value close to the minimum value) occurring in each cluster of samples that fall below the threshold value(s).

Instead of steps, the algorithm can also be designed in terms of strides. This can be advantageous in case of asymmetric walking patterns (so-called period-2 signals). A step is the displacement of one foot, a stride is the displacement of both (one step with the left foot, one step with the right foot). When the accelerometer 6 is located at the foot or ankle, there will be strong peaks evident in the accelerometer measurements when the corresponding foot is moving, and a little 'cross talk' when the other foot is moving. When the accelerometer 6 is located at the torso, the movements of both feet will produce similar accelerometer signals. An accelerometer 6 located on the side of the body may show some asymmetry in the accelerometer measurements.

Figure 8:
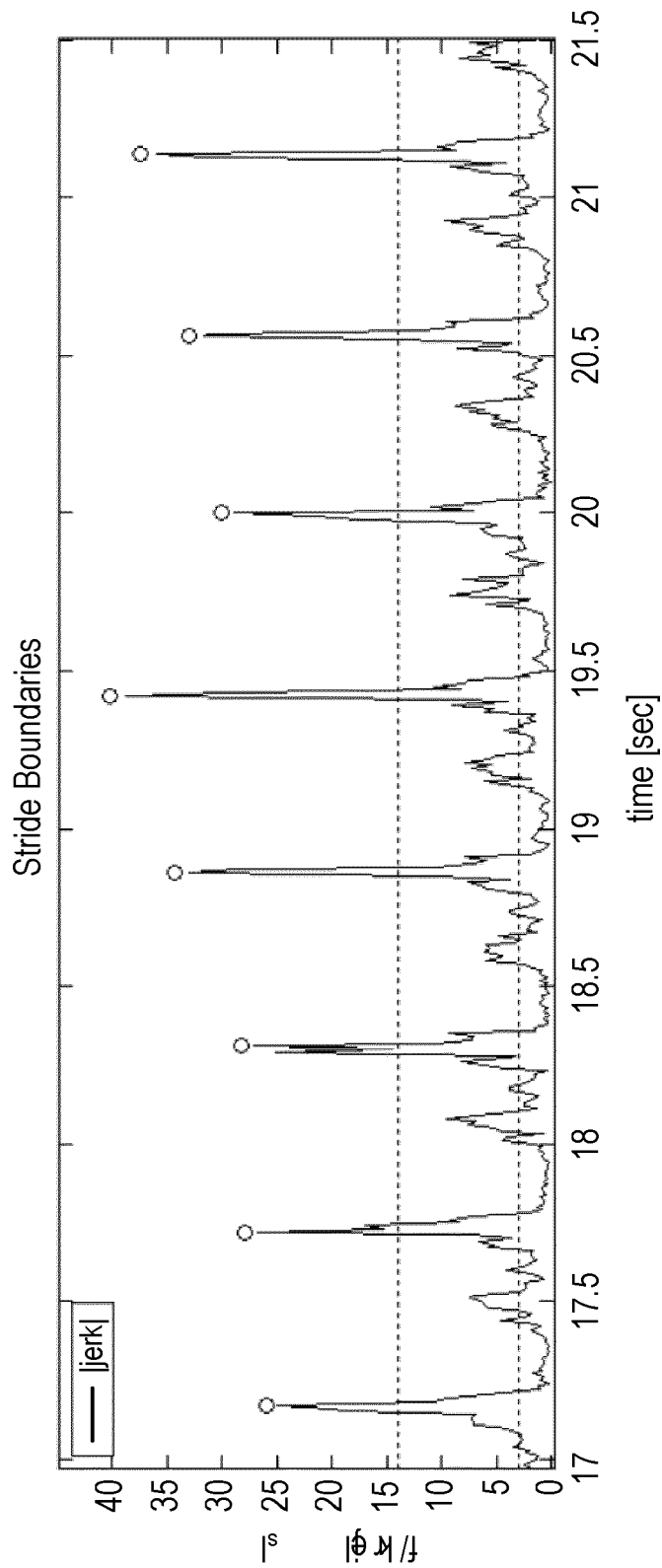
FIG. 8 is a plot illustrating the derivative of measurements from an accelerometer that is worn on a user's ankle.

Alternatively, as noted above, for an accelerometer 6 located on the lower body of the user 4, the jerk can be determined by determining the derivative of the acceleration signal and the jerk can be analysed to identify clusters as described above. The graph in FIG. 8 illustrates an exemplary jerk signal with identified stride boundaries marked.

One problem that has been found with the above techniques is that acceleration signals often contain multiple peaks per step (i.e. per heel strike), or even random peaks that occur between steps by the user 4. If it is assumed that the user 4 has a steady cadence (i.e. a steady rate of steps), then these multiple peaks and random peaks can be filtered out from the resulting step series by removing steps that severely influence the overall step time variability. This filtering is described in more detail below with reference to a later aspect of the invention. Once step boundaries have been identified in the accelerometer signal, a 'step time' can be derived, which is the time between two consecutive identified steps when the accelerometer measurements are collected on the torso of the user 4 or two consecutive identified strides when the accelerometer measurements are collected at the feet or ankle of the user 4. For clarity, the moment of a single step is referred to as the 'step peak' or 'heel strike', so the step time in some implementations is the time between two step peaks. The found step times are tested for regularity. In particular, each step time is analysed to determine if the gap between the steps or strides (represented by the step time) is too long and should in fact be considered to be a gap between different walking parts. In one particular implementation, if a central stepping time (e.g. an average (mean or median) of the step times) is $T_{step}$ seconds, then if there is no step detected in a time (for example given by Threshold$_{step}$*$T_{step}$) seconds, the end boundary of a walking part is found at that last step. The use of this time threshold (Threshold$_{step}$*$T_{step}$) is advantageous as it adapts the boundary to the speed a particular user 4 is walking, although a fixed, user-independent, time threshold could be used if desired. A similar method is used to delineate the start of a walking part. A preferred value for Threshold$_{step}$ is 4.

One aspect of the invention provides a modification to the step detection. In particular, the threshold (or thresholds if two thresholds are used to identify a cluster) used to identify extrema (i.e. maxima or minima) corresponding to step boundaries (depending on the position of the accelerometer 6 on the user's body) is adapted according to characteristics of the acceleration (or jerk) signal. Adapting the threshold in this way to the signal allows step boundaries to be detected more reliably, for example since the maximum or minimum acceleration experienced by the accelerometer 6 during a heel strike can change over time due to changes in the positioning of the device 2 relative to the user's body. Adapting the threshold also allows the algorithm to better adapt to characteristics of a particular user 4 (for example a user that has a particularly heavy or light heel strike) or the surface that the user 4 is walking on.

Figure 9:
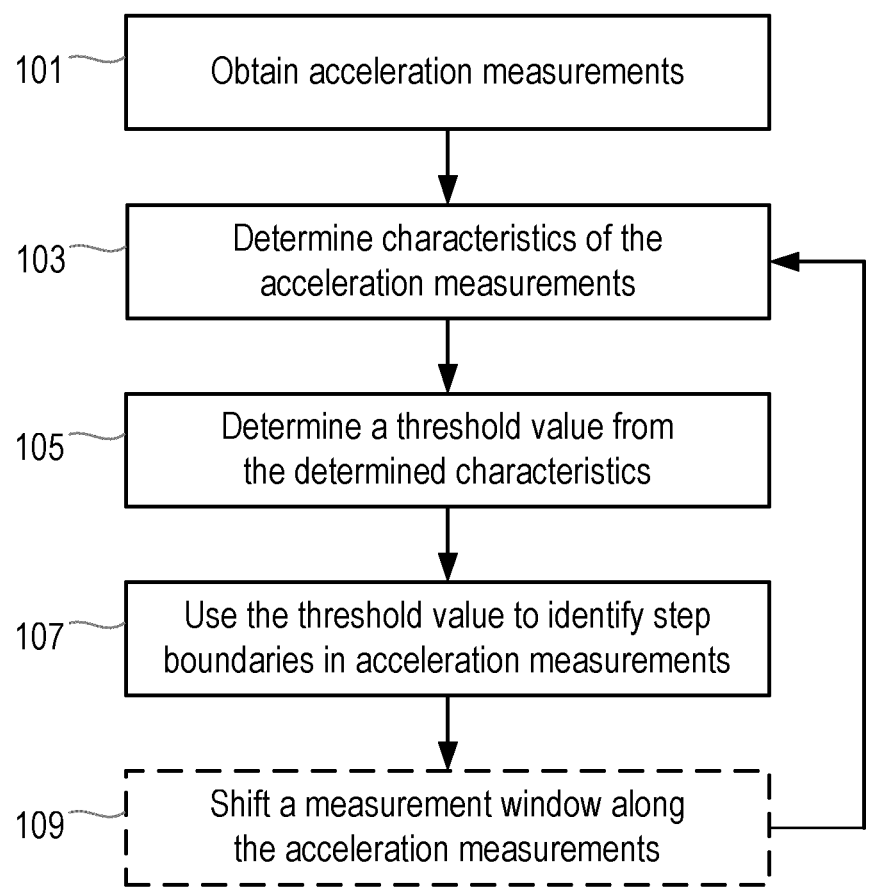
FIG. 9 is a flow chart illustrating a method according to an aspect of the invention.

A flow chart illustrating a method of processing acceleration measurements to identify step boundaries according to this aspect of the invention is shown in FIG. 9. In the first step, step 101, acceleration measurements are obtained using an accelerometer 6 attached to or worn by the user 4.

In step 103, one or more characteristics of the acceleration measurements are determined. In some embodiments, the characteristics include the mean of the acceleration measurements and/or the standard deviation of the measurements, although higher order moments and/or signal per sensor axis could also or alternatively be used, for example.

Then, in step 105, a threshold value that is to be used to identify step boundaries in the acceleration measurements is determined from the one or more characteristics of the acceleration measurements.

The determined threshold value is then used to identify step boundaries in the acceleration measurements (step 107). As described above, the threshold value can be used to identify clusters of measurement samples that exceed the threshold value, with the step boundaries in some embodiments being given by the peak or minimum in each identified cluster.

Thus this method results in the threshold used for step boundary detection being adapted based on the characteristics of the acceleration signal.

It will be appreciated that in accordance with the various embodiments described above, the method can further comprise combining the acceleration measurements on the three axes, taking the norm of the combined acceleration measurements, determining the derivative of the combined acceleration measurements (i.e. determining the jerk), taking the derivative of the measurements on the three axes and combining the derivatives to determine the jerk or determining the derivative of the combined acceleration measurements and taking the norm of the result (i.e. determining |jerk|), and any one or more of steps 103, 105 and 107 can be performed on the norm of the acceleration measurements, the jerk or the norm of the jerk. It will be appreciated that taking the norm of a signal can be performed in any known manner, for example by computing an Euclidian distance (or L2 norm) or Manhattan distance (or L1 norm—summing the absolute values of the three axes).

In some embodiments the characteristics are calculated in step 103 for a subset of the measurements (e.g. a 20-second window) and the threshold derived from the characteristics is applied to the measurements in that window to identify step boundaries. The window can then be shifted (step 109) along the acceleration measurements (e.g. by a predetermined amount, such as half the window length—10 seconds or more, but with some overlap between consecutive positions of the window, or the equivalent number of acceleration samples), and steps 103, 105 and 107 are repeated for the new set of measurements in the window.

In a specific embodiment, the threshold is adapted by using the mean and the standard deviation of the signal (e.g. the norm of the acceleration or norm of the jerk). The mean and standard deviation are computed over a window of, for example, 20 seconds duration. The threshold for identifying clusters in an acceleration, norm of acceleration, jerk or norm of jerk signal is given by a function of the mean and standard deviation for the window. In some embodiments, the threshold for a |acc| signal is given by:

$$stepThres=|grav|+ThresFac*(stepMean-|grav|+stepStd); \quad (1)$$

where |grav| is the value of gravity (9.81 ms$^{-2}$), ThresFac is a constant (e.g. having a value of 1.1 or 0.9), stepMean is the mean of the signal and stepStd is the standard deviation of the signal.

In some embodiments, the thresholds used to identify clusters in a jerk signal are given by:

$$strideThresIn=strideMean+ThresFacIn*strideStd; \quad (2)$$

$$strideThresOut=strideMean-ThresFacOut*strideStd; \quad (2)$$

where ThresFacIn and ThresFacOut are constants (e.g. having a value of 1.7 and 0.2 respectively), strideMean is the mean of the signal and strideStd is the standard deviation of the signal.

In alternative embodiments, the threshold or thresholds used to identify clusters in an acceleration or jerk signal could be determined using, for example, regression models.

As described above, the thresholds determined from the characteristics of the signal are applied to the signal to identify the steps (or strides) as the maximum or minimum value in a cluster of samples. The first step and last step determine a walking part. The first step and last step can be determined as described above, for example if there is no step detected in a time (Threshold$_{step}$*T$_{step}$) seconds after the current step, the end boundary of a walking part is found at that last step.

Optionally, using the identified walking part, a new value for the central steptime is computed as the median of all step times in the walking part. The identified walking part gives a better delineation of the part of the signal that is of interest, and thus the estimation of the central steptime is based on a better delineated data set (so the effect of outliers is reduced, giving a better estimate of the central steptime). This steptime is used to set the parameters for detecting clusters. Also, the above thresholds are recomputed, using only the part of the signal that is within the identified walking part. Last, the step peaks are identified by searching within the walking part, using the new parameter and threshold values. In this way, the step peaks for a walking part can be refined to improve the walking detection.

It will be appreciated that the threshold adaptation described above can be performed in a customization or configuration mode of the device 2 when the device 2 is first switched on or first used by user 4. In this case, measurements of acceleration can be obtained and processed to determine the threshold(s) as described above, and those threshold values can be applied to measurements of acceleration obtained during later use of the device 2 by the user 4 to identify the user's steps.

Another aspect of the invention provides that after identifying steps (and in particular the times at which the steps have occurred) in the acceleration signal, the steps are tested for step time regularity. This aspect of the invention can be applied to steps identified using the techniques described in WO 2011/004322 or the techniques described above.

It has been found that when using a threshold to detect peaks as described above (and even where the threshold is adapted to the characteristics of the acceleration signal), some peaks corresponding to steps can be missed because the magnitude of the acceleration or jerk at the time of the step does not pass the threshold. In other cases, two peaks can be found for a single step because the acceleration signal happens to fall below the threshold for longer than the threshold time (threshold$_{gap}$) leading to multiple clusters being identified and hence to multiple step peaks. Even with threshold adaptation, finding an optimal threshold might be difficult given the range within which signal strength/energy may vary; and there may still be missed and duplicate steps. According to this aspect of the invention, since it is desired to identify parts of the acceleration signal that correspond to walking of the user (rather than to generally classify the acceleration signal as any one of a number of different activities), it is assumed that when the user 4 is walking the steps will occur regularly. Thus, by assuming regularity, steps that have been missed by the threshold detection or duplicated step peaks can be corrected.

Figure 10:
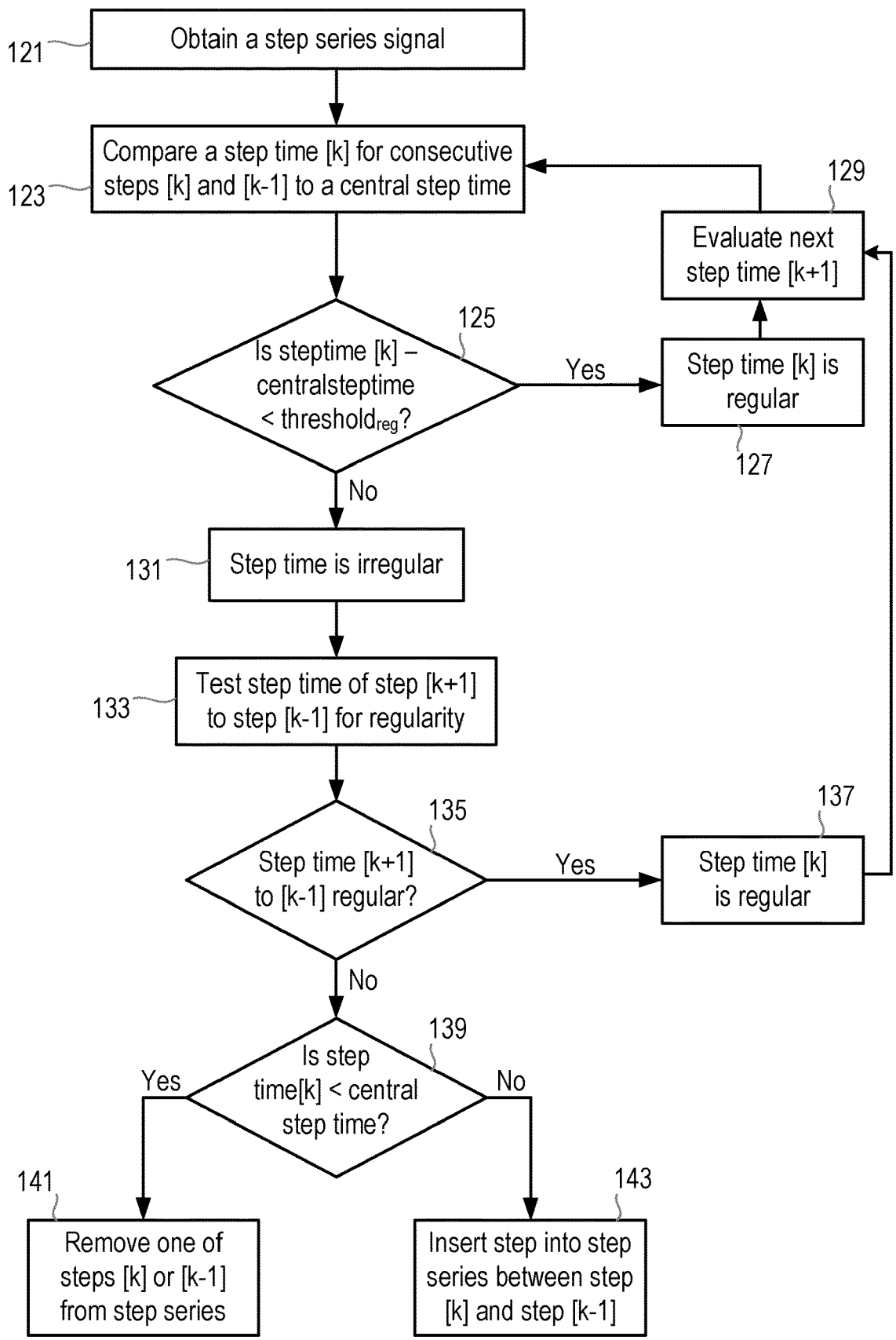
FIG. 10 is a flow chart illustrating a method according to another aspect of the invention.

A flow chart illustrating an exemplary method of correcting the regularity is shown in FIG. 10. In the first step, a step series signal is obtained that indicates the times at which steps have been detected. This step series signal can be obtained using any of the techniques described above.

Taking each step in turn, the step time (the time between the current step peak and the previous step peak) is compared to the central step time (step 123). If the step time is within a threshold amount (threshold$_{reg}$) of the central step time (step 125), the step time is considered to be a regular step time (step 127), and the next step and hence next step time is evaluated (step 129). In some embodiments the threshold corresponds to the cluster size (which is the number used to identify the size/duration of the cluster where the signal (e.g. |acc|) passes the threshold). The cluster size is typically half the step time.

Even if the step time is found in step 125 to be irregular (step 131), it is possible that a subsequent step is regular, in which case the step time between the next step and the previous step is compared to the threshold (i.e. threshold$_{reg}$) (steps 133 and 135).

For example, if the current step is step[k] (which represents the time at which step[k] occurred) and the step time from the previous step, step[k-1], to step[k] is steptime[k] (which has been found to be irregular), then it is determined if:

$$|(step[k+1]-step[k-1]-2*CentralStepTime)|<threshold_{reg} \quad (4)$$

If the result of evaluating (4) is true, then the step time from step[k-1] to step[k+1] is found to be regular and thus steptime[k] is found to be regular (step 137). The next step time is then evaluated (step 129).

If the result of evaluating (4) is false, then the current step time is considered irregular and it is necessary to either delete a step from the step series or insert a step into the step series. To determine which is required, the step time[k] is compared to the central step time (step 139).

A deletion is needed when the current step time (steptime [k]) is less than the central step time (step 141). In this case, one of the two steps for steptime[k] (i.e. step [k] or [k-1] is to be removed). The decision on which of the steps to remove can be based on one of several rules. In one rule, the step with the smallest magnitude is removed. However, this rule may lead to a resulting step time (between the remaining step and its new neighbouring step) that is too large according to the regularity test, in which case if the regularity test is failed, the other step (i.e. the one with the largest magnitude) is removed instead.

An insertion is needed when the current step time (step-time[k]) is larger than the central step time (step 143). A step peak can be inserted at the maximum of the step series signal (or minimum as appropriate) in a range of one central step time in duration. The start of the range can be found as one cluster size after the previous step (step[k-1]). In some cases the insertion process can be repeated if the step time between the inserted step and the next step is still beyond the regularity margin (since the spurt can be delineated at (typically) 4 step times, this insertion process stops at that boundary).

Another method to correct for irregular step times (as an alternative to the above method) is to observe the variance in the series of step times. In a iterative manner, the two steps (peaks) that constitute the smallest step time are searched. Given those two steps, three variances are computed: the variance of the given series of step times, the variance of the series when the first of the two steps is omitted, and the variance of the series when the second of the two steps is omitted. If the first variance is the smallest of the three, then the iteration process is stopped. If the second variance is the smallest, then the first of the two steps is removed from the step series. If the second variance is the smallest, then the second of the two steps is removed from the step series. The iteration process is then repeated with the new step series. It should be noted that this decision rule to select the step to be removed can also be used in the first regularity test described above.

As described above with reference to FIG. 3, after the step detection algorithms 20 have detected the steps in the accelerometer measurements, the step series is passed to a second block 22 that discards series of identified steps that do not have a sufficient duration to be considered walking. In particular, in block 22 the duration of each walking part identified in the step series is compared to a threshold (a minimum duration). Any walking part whose duration does not exceed the threshold is discarded. An exemplary minimum duration can be 10 seconds, although other values can be used. The step series for any walking part that does exceed the minimum duration is passed to the third block 24 as a candidate walking part where it is validated in order to filter out walking parts corresponding to user activities that are not walking or that correspond to abnormal walking.

Figure 11:
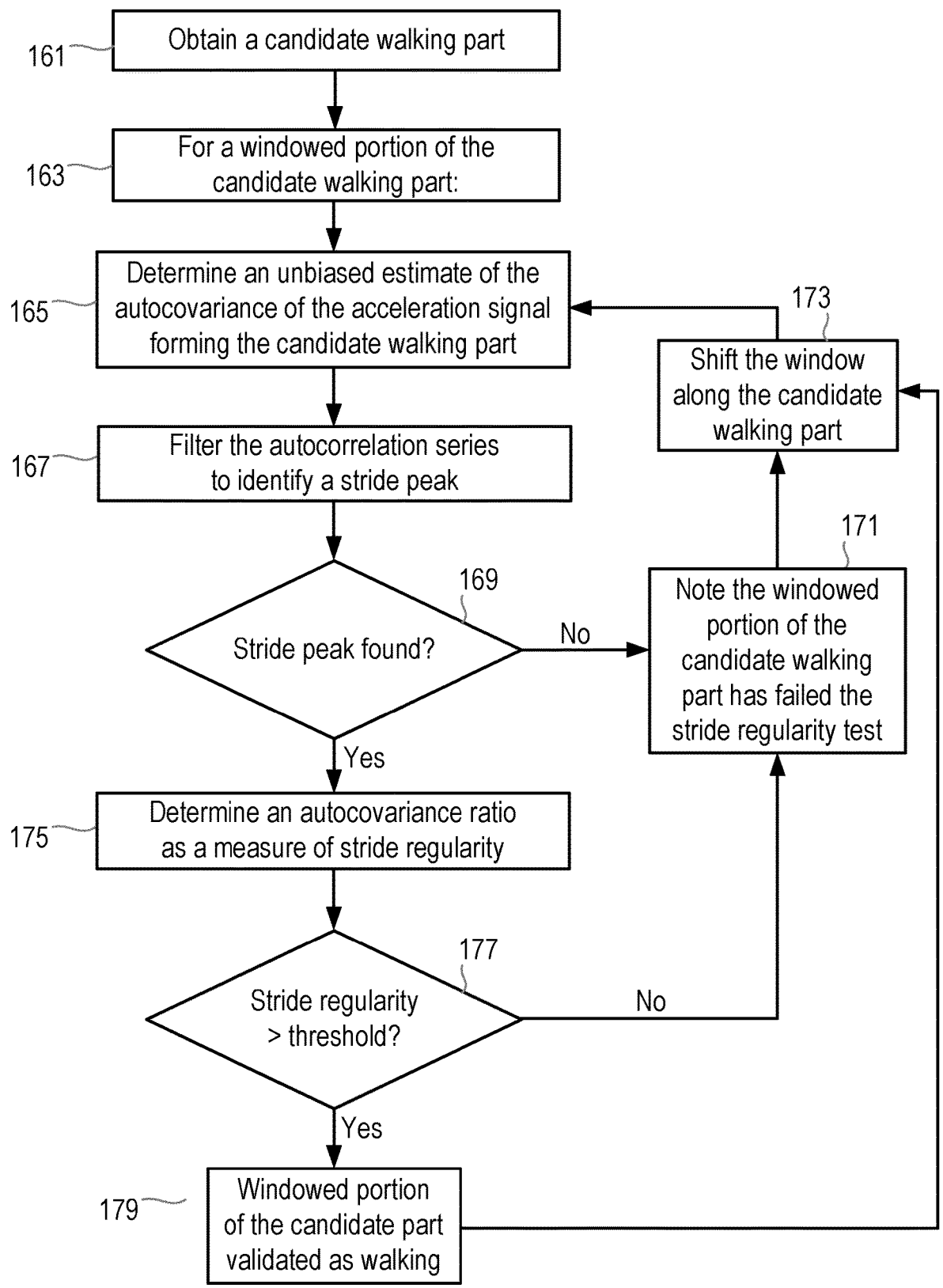
FIG. 11 is a flow chart illustrating a method according to another aspect of the invention.

According to yet another aspect of the invention, a first type of validation comprises identifying walking parts with a stride time with a certain regularity and where the signal shape of each stride is similar. This aspect of the invention can be applied to steps identified using the techniques described in WO 2011/004322 or the improved techniques described above. The flow chart in FIG. 11 illustrates a method of performing the validation according to this aspect of the invention. It should be noted that in the previous aspect, stride regularity was assumed in order to remove spurious steps or add missed steps, but in the present aspect, the regularity of the found steps is tested (i.e. regularity is not assumed as in the previous aspect).

In this aspect, the stride regularity of the walking part is evaluated locally (which can include a windowed portion of the walking part, as described in the specific embodiment below, or the whole walking part). The stride regularity can be measured by analysing the autocorrelation of the walking part. In particular, for a candidate walking part obtained as described above (step 161), a local portion of the walking part is selected for analysis, for example by applying a window to the walking part (step 163). The window can have a width of, for example, 5 seconds, although other widths can be used.

In step 165, the autocorrelation of the local portion of the acceleration measurements corresponding to the local portion of the walking part is determined. The autocorrelation can be computed over the normalized acceleration, or over any of the separate x-, y- or z-axes. In some embodiments, the autocorrelation is computed by taking the unbiased estimate of the autocovariance over the acceleration signal corresponding to the windowed portion of the candidate walking part.

Figure 12:
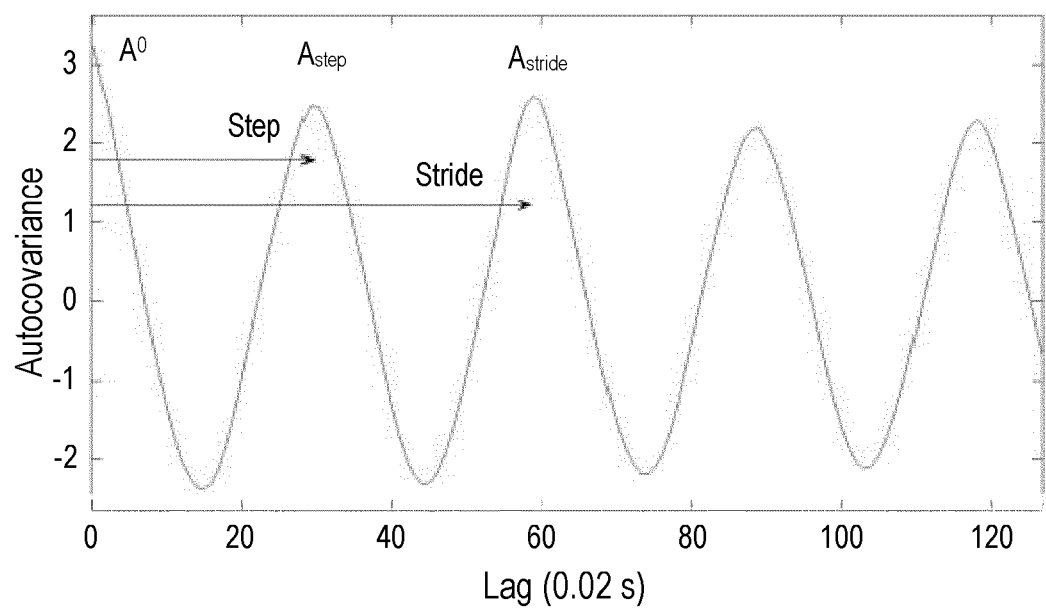
FIG. 12 is a graph illustrating the auto correlation of a regular gait.

Next, in step 167, the autocorrelation series determined in step 165 is filtered to identify a stride peak. FIG. 12 illustrates an exemplary autocorrelation signal for an accelerometer located on the user's torso where steps from the left and right feet appear as similar signals with three labelled peaks: $A_0$, which corresponds to the autocorrelation (autocovariance) at zero lag, $A_{step}$, which corresponds to the step peak (also referred to as the first peak), and $A_{stride}$ which corresponds to the stride peak (also referred to as the second peak). Period-2 type signals would have a larger stride peak.

In some embodiments, step 167 comprises using a moving average filter, for example with a window width of 0.16 seconds, to identify a stride peak. The central moving average filter helps to smooth the signal to make the identification of the stride peak, $A_{stride}$, more reliable since the unfiltered autocorrelation signal often has multiple peaks.

If no stride peak can be found in the filtered autocorrelation series (step 169) then this implies that the local (e.g. windowed) portion of the candidate walking part either does not correspond to walking or contains an abnormal (e.g. disturbed) walk. The local portion of the candidate walking part is therefore noted as failing the stride regularity test (step 171).

Another local part of the candidate walking part is then analysed, for example by shifting the window on the candidate walking part along the signal (step 173), for example by 0.1 seconds, and the method returns to step 165 and repeats for the new windowed portion of the signal.

It will be noted that although the local portion of the candidate walking part may be noted as having failed the stride regularity test in step 171, the portion is not yet discarded, as it is possible that although the portion failed the test, an overlapping portion of the signal (for example in a portion in a window shifted by 0.1 seconds) may pass the stride regularity test. Once all local (e.g. windowed) portions have been tested, decisions can be taken on whether any parts of the candidate walking part can be discarded.

If a stride peak is found in step 169), then in step 175 an autocovariance ratio is calculated (as described by R. Moe-Nilssen and J. L. Helbostad in "Estimation of gait cycle characteristics by trunk accelerometry" Journal of Biomechanics, vol. 37, no. 1, pp. 121-126, 2004) which is given by $$\frac{A_{stride}}{A_0},$$

with the autocovariance ratio expressing the stride regularity.

The stride regularity (given by the autocovariance ratio) is then compared to a threshold (step 177). A default minimum stride regularity threshold that can be used is 0.5, which has been found to be a good trade-off between sensitivity and precision. The precision of the walking detection can be generally increased by raising the threshold, but this reduces the sensitivity of the walking detection.

Validating the stride regularity locally (e.g. within a windowed portion of the candidate walking part) allows for a variable pace during a walk, and according to the above method, a walk is considered to be regular when it is locally regular during each point in time. Portions of a walking part can be considered sufficiently regular when the local pace (i.e. the stride regularity) has not changed by too much within the windowed (e.g. 5 seconds) portion. If the stride regularity for a portion is found to fall below the threshold in step 177, the portion is noted as having failed the stride regularity test (step 171). If the stride regularity for a portion is found to exceed the threshold, the portion is validated as walking (step 179) and the window is shifted along the candidate walking part (step 173).

Where following the evaluation of the candidate walking part a part (e.g. a portion) is discarded, this results in the candidate walking part being split into two separate walking parts. The new separate walking parts can then be tested to determine if they have a sufficient duration to be considered walking parts (as described above for block 22), and if not, one or both of the separate walking parts can be discarded as well.

Although the above stride regularity validation step filters out activities having an irregular pattern, other factors or activities like running and the heartbeat of a user 4 can have regularities similar to walking, and walking parts that actually correspond to these factors or activities can pass the stride regularity validation. Therefore, in accordance with another aspect of the invention, a validation test is provided that aims to identify and exclude these walking parts. In particular, the types of activities that pass the earlier step detection and the first validation stage (if applied) and that do not correspond to walking by the user 4 generally have a different movement vigour to walking Therefore, according to this aspect of the invention, the movement vigour of a walking part is calculated and the movement vigour is compared to one or more thresholds or an allowable range and any walking part that does not meet the threshold(s) or fall within the allowable range is discarded. This aspect of the invention can be applied to steps identified using the techniques described in WO 2011/004322 or the improved techniques described above.

In one embodiment, movement vigour (also referred to as activity level herein) can be calculated from the variance of the acceleration along each of the x-, y-, and z-axes using:

$$\text{Activity level} = 10 * \log_{10}(\text{var}(acc_x) + \text{var}(acc_y) + \text{var}(acc_z)) \quad (5)$$

In this embodiment, if the activity level does not fall within an acceptable range then the walking part is discarded. An exemplary acceptable range for the activity level calculated according to equation (5) is [5.8, 20.5], although it will be appreciated that other ranges can be used.

In some embodiments, a measure of the energy in the signal could be given simply by the sum of the variances of the acceleration along each of the x-, y- and z-axes. In alternative embodiments, other measures of the energy of the acceleration signal can be used in place of the activity level equation given above.

The activity level or other measure of the energy of the signal can be calculated for the whole of the candidate walking part or a windowed portion of the candidate walking part (with the window being the same size as or a different size to the window used in the stride regularity embodiment described above).

Another type of activity that often passes the above stride regularity validation and movement vigour validation and that should not necessarily be considered to be walking is when the user 4 is walking up or down stairs. Walking up or down stairs has a regular movement pattern and vigour that is similar to walking on level ground, but in many cases (for example when the detected walking parts are to be analysed to determine a fall risk of the user 4), candidate walking parts or parts of candidate walking parts that correspond to stair walking should be discarded. Therefore a further aspect of the invention provides that the candidate walking parts are analysed to determine whether they correspond to stair walking. In particular, measurements from an air pressure sensor 12 are collected and used to determine a change in height of the device 2, and if there has been a change in height of the device 2 consistent with a user ascending or descending stairs (or walking up or down a slope), then the walking part can be discarded. This aspect of the invention can be applied to steps identified using the techniques described in WO 2011/004322 or the improved techniques described above.

Figure 13:
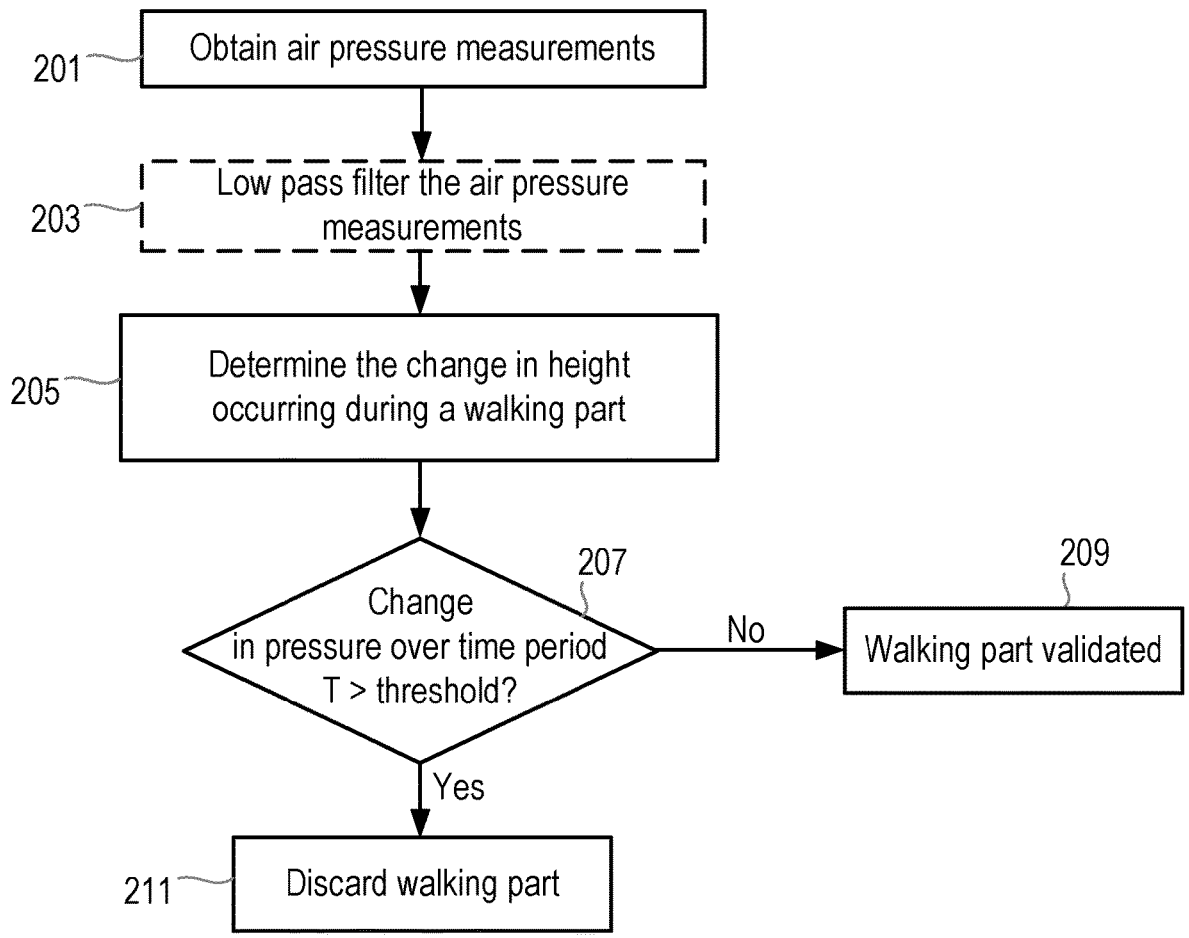
FIG. 13 is a flow chart illustrating a method according to another aspect of the invention.

A flow chart illustrating a method in accordance with the further aspect is shown in FIG. 13. In a first step, step 201, measurements from an air pressure sensor 12 are obtained while the acceleration measurements are being obtained. Next, (optionally), the air pressure measurements are low-pass filtered to smooth the effect of short-term fluctuations in the air pressure (step 203). This can be done using a Butterworth filter, for example. The cut-off frequency for the filter may be ⅛ Hz, for example.

In step 205, the air pressure measurements are processed to determine a change in height of the device 2 during a particular candidate walking part. Step 205 comprises processing the part of the air pressure measurements corresponding in time to the candidate walking part. Changes in air pressure can indicate a change in altitude or height. Although those skilled in the art will be aware of suitable techniques/equations for converting an air pressure or change in air pressure into an altitude/height measurement or change in altitude/height measurement, in preferred embodiments a conversion of the air pressure or change in air pressure into height or a change in height is not required since changes in the air pressure signal reflect the changes in height.

In the context of a user-worn device 2, apparent changes in height over a short period of time can be due to disturbances in the air (e.g. wind, a door opening or closing, etc.), so only pressure changes (and thus height changes) that last a sufficient duration and are of a significant magnitude are considered as stair walking.

Thus, in step 205 a filter is applied to the air pressure signal to filter out short term changes in pressure which likely do not indicate an actual change in height of the device 2. In some embodiments a linear-phase filter is used, such as a Moving Average (MA) filter. However, since the measurements from an air pressure sensor 12 may show peaks of short duration, the use of a non-linear filter, such as a median filter, is preferred. A half-window size of 2 seconds for the median filter is preferred.

The signal output by the filter represents the long-term height, excluding short term air pressure changes (for example caused by wind or doors opening or closing). The (absolute) change in pressure over some time period T is compared to a threshold value (step 207). For example, the threshold can have a value of 0.1 hPa over a time period T of 3 seconds. If the (absolute) change in pressure over some time period T is less than the threshold value then the walking part is not considered to relate to the user 4 walking up or down stairs, and the walking part is validated as walking (step 209).

If the (absolute) change in pressure over some time period T is greater than the threshold value then the walking part is considered to relate to the user 4 walking up or down stairs, and the walking part (or the part of the walking part in which the change in pressure occurs) is discarded (step 211). In some embodiments, regions or parts of candidate walking parts that are considered to be stair walking can have an additional safety margin of 1 second (or a similar timescale) before and after the region discarded as a precaution since a user 4 may change their gait slightly before the first step on the stairs and/or the initial change point in pressure may not be picked up by the processing described above.

It will be appreciated that any of the above aspects of the invention can be used in isolation or in combination to improve the accuracy of existing walking detection algorithms.

The effectiveness of the above aspects of the invention in improving the performance of the step/walking detection algorithm in WO 2011/004322 is illustrated below in Table 1. It has been found that the algorithm described in WO 2011/004322 has a sensitivity of 66.1% and a precision of 98.2% (with sensitivity representing the percentage of walking by the user that is identified as such, and precision representing the reliability of the detection; i.e. how often the walk detection was correct out of the walking parts the algorithm had found). Acceleration measurements were obtained for five users who performed regular daily activities for one or two days. The acceleration measurements were then processed according to the algorithm described in WO 2011/004322 with the modifications provided by the aspects of the invention described above. As shown in Table 1, the modifications increase the sensitivity to 80.1% and the precision to 99.9%. The precision can be further increased by raising the minimum stride regularity threshold, in exchange for a lower sensitivity.

TABLE 1

| Subject | Recording time | Detected walk time | Sensitivity | Precision, reliability |
|---|---|---|---|---|
| 1 | 8.5 h | 00:09:31 | 80.3% | 99.9% |
| 2 | 11.2 h | 00:45:44 | 69.3% | 99.7% |
| 3 | 11.8 h | 00:31:14 | 93.4% | 99.8% |
| 4 | 9.1 h | 00:22:57 | 75.2% | 100% |
| 5 | 6.9 h | 00:12:28 | 84.7% | 99.9% |
| Total | 47.6 h | 02:01:55 | 80.1% | 99.9% |

It will be appreciated that although the processing unit 8 is only described herein as processing the acceleration measurements to identify when the user 4 is walking, in practical implementations of a device 2 or activity monitor the processing unit 8 can also execute algorithms to determine when the user 4 is running/jogging, jumping, performing sit-to-stand/stand-to-sit movements (i.e. standing up from a seated position/sitting down on a chair), walking up or down stairs, getting into/out of bed, etc. In addition or alternatively, the processing unit 8 may process the acceleration measurements to detect whether the user 4 has suffered a fall.

There are therefore provided several improvements to existing walking detection algorithms that provide increased sensitivity and precision in identifying walking by a user of a device.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of processing measurements of acceleration to identify steps by a user, the method comprising:
    measuring, with an accelerometer of an activity monitor worn or carried by a user, values of acceleration of the activity monitor, wherein the measured values provide a signal with measurements of acceleration;
    analyzing, with a processor of the activity monitor, the measurements of acceleration to determine a value for a threshold that is to be used to identify a series steps by the user in the measurements of acceleration;
    using, with the processor of the activity monitor, the determined value for the threshold to identify the series of steps by the user in the measurements of acceleration;
    testing, with the processor of the activity monitor, the identified series of steps for regularity, including:
        determining a step time for each pair of consecutive steps in the series of steps based on the time between the consecutive steps;
        determining a central step time based on an average of the determined step times; and
        identifying the step time of a pair of consecutive steps as irregular based on the step time and a threshold amount of the central step time;
    inserting, with the processor of the activity monitor, a new step by the user to the series of steps based on the step time being irregular and a step by the user being missed; and
    removing, with the processor of the activity monitor, an existing step by the user from the series of steps based on the step time being irregular and there is a duplicated step by the user.

2. The method as claimed in claim 1, wherein the step of testing the identified steps for regularity comprises:
    identifying the step time as regular if the step time is within the threshold amount of the central step time.

3. The method as claimed in claim 2, wherein the step of testing the identified steps for regularity further comprises:
    if a step time for a particular pair of consecutive steps is not within a threshold amount of the central step time, determining the step time between one of the pair of consecutive steps and a step neighboring the other one of the pair of consecutive steps;
    identifying the step time for the particular pair of consecutive steps as regular if the determined step time between the one of the pair of consecutive steps and the step neighboring the other one of the pair of consecutive steps is within a threshold amount of twice the central step time; and
    otherwise identifying the step time for the particular pair of consecutive steps as irregular.

4. The method as claimed in claim 2, wherein the step of testing the identified steps for regularity further comprises:
    if the step time for a particular pair of consecutive steps is identified as irregular, comparing the step time to the central step time;
    determining that a step between the pair of consecutive steps has been missed if the step time is greater than the central step time; and
    determining that a step in the pair of consecutive steps is a duplicate if the step time is less than the central step time.

5. A method of processing measurements of acceleration to identify steps by a user, the method comprising:
    measuring, with an accelerometer of an activity monitor worn or carried by a user, values of acceleration of the activity monitor, wherein the measured values provide a signal with measurements of acceleration;
    analyzing, with a processor of the activity monitor, the measurements of acceleration to determine a value for a threshold that is to be used to identify a series steps by the user in the measurements of acceleration;
    using, with the processor of the activity monitor, the determined value for the threshold to identify the series of steps by the user in the measurements of acceleration;
    testing, with the processor of the activity monitor, the identified series of steps for regularity, including:
        determining a step time for each pair of consecutive steps in the series of steps as the time between the consecutive steps;
        for the smallest determined step time, computing a first variance as the variance of the step times for each pair of consecutive steps, computing a second variance as the variance of the step times when the first step forming the pair of steps with the smallest determined step time is omitted, and computing a third variance as the variance of the step times when the second step forming the pair of steps with the smallest determined step time is omitted;
        determining that the first step forming the pair of steps with the smallest determined step time is a duplicate if the second variance is the smallest variance of the first variance, the second variance and the third variance; and
        determining that the second step forming the pair of steps with the smallest determined step time is a duplicate if the third variance is the smallest variance of the first variance, the second variance and the third variance; and
    removing, with the processor of the activity monitor, an existing step by the user from the series of steps if it is determined from a result of the step of testing that there is a duplicated step by the user.

6. The method as claimed in claim 5, further comprising:
    inserting, with the processor of the activity monitor, a new step by the user to the series of steps if it is determined from the result of the step of testing that a step by the user has been missed.

7. The method as claimed in claim 1, further comprising the steps of:
    identifying a first step and a last step for a walking part from the steps identified in the measurements of acceleration; and
    repeating the steps of analyzing and using on the measurements of acceleration corresponding to the walking part to identify steps by the user.

8. The method as claimed in claim 1, wherein, for a walking part comprising a series of steps identified in the measurements of acceleration, the method further comprises:
determining an activity level for the user from the measurements of acceleration corresponding to the walking part; and
discarding the walking part if the activity level of the user indicates that the user is not walking.

9. The method as claimed in claim 1, wherein, for a walking part comprising a series of steps identified in the measurements of acceleration, the method further comprises:
determining if the walking part corresponds to the user walking up or down stairs; and
discarding the walking part if it is determined that the walking part corresponds to the user walking up or down stairs.

10. The method as claimed in claim 9, wherein the step of determining if the walking part corresponds to the user walking up or down stairs comprises:
obtaining measurements of an air pressure from the device worn or carried by the user; and
processing the obtained measurements of air pressure to determine if there has been a change in height consistent with the user walking up or down stairs during the walking part.

11. A computer program product having computer readable code embodied therein, the computer readable code being configured such that, on execution by a suitable processing unit or computer, the processing unit or computer performs the method according to claim 1.

12. An apparatus for processing measurements of acceleration to identify steps by a user, the apparatus comprising:
a processing unit configured to
obtain measurements of acceleration from a device worn or carried by a user;
analyze the measurements of acceleration to determine a value for a threshold that is to be used to identify steps by the user in measurements of acceleration;
use the determined value for the threshold to identify a series steps by the user in the measurements of acceleration;
test the identified series of steps for regularity by:
determining a step time for each pair of consecutive steps in the series of steps based on the time between the consecutive steps;
determining a central step time based on an average of the determined step times; and
identifying the step time of a pair of consecutive steps as irregular based on the step time and a threshold amount of the central step time;
insert a new step by the user to the series of steps if it is determined from a result of the testing that the step time is irregular and a step by the user has been missed; and
remove an existing step by the user from the series of steps if it is determined from the result of the testing that the step time is irregular and there is a duplicated step by the user.

13. The apparatus as claimed in claim 12, wherein the processing unit is further configured to evaluate a stride regularity of the series of steps.

14. The apparatus as claimed in claim 12, wherein the processing unit is further configured to:
determine if the series of steps corresponds to the user walking up or down stairs; and
discard the series of steps if it is determined that the series of steps corresponds to the user walking up or down stairs.

15. A device that is to be worn or carried by a user, the device comprising:
an accelerometer for providing measurements of acceleration; and
an apparatus as claimed in claim 12.

16. The method as claimed in claim 5, wherein the step of analyzing the measurements of acceleration comprises:
determining one or more characteristics from the measurements of acceleration; and
determining a value for a threshold that is to be used to identify steps by the user from the one or more characteristics.

17. The method as claimed in claim 5, further comprising the steps of:
identifying a first step and a last step for a walking part from the steps identified in the measurements of acceleration;
repeating the steps of analyzing and using on the measurements of acceleration corresponding to the walking part to identify steps by the user.

18. The method as claimed in claim 5, wherein, for a walking part comprising a series of steps identified in the measurements of acceleration, the method further comprises:
determining an activity level for the user from the measurements of acceleration corresponding to the walking part; and
discarding the walking part if the activity level of the user indicates that the user is not walking.

19. The method as claimed in claim 5, wherein, for a walking part comprising a series of steps identified in the measurements of acceleration, the method further comprises:
determining if the walking part corresponds to the user walking up or down stairs; and
discarding the walking part if it is determined that the walking part corresponds to the user walking up or down stairs.

20. The method as claimed in claim 19, wherein the step of determining if the walking part corresponds to the user walking up or down stairs comprises:
obtaining measurements of an air pressure from the device worn or carried by the user; and
processing the obtained measurements of air pressure to determine if there has been a change in height consistent with the user walking up or down stairs during the walking part.

* * * * *